(12) United States Patent
Nappa et al.

(10) Patent No.: US 8,586,804 B2
(45) Date of Patent: Nov. 19, 2013

(54) SYNTHESIS OF 1,1,3-TRICHLORO-1-PROPENE

(75) Inventors: Mario Joseph Nappa, Newark, DE (US); Robert D. Lousenberg, Wilmington, DE (US); Andrew Jackson, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/278,511

(22) Filed: Oct. 21, 2011

(65) Prior Publication Data

US 2012/0142980 A1 Jun. 7, 2012

Related U.S. Application Data

(60) Provisional application No. 61/418,566, filed on Dec. 1, 2010.

(51) Int. Cl.
*C07C 17/25* (2006.01)

(52) U.S. Cl.
USPC .......................................... 570/227; 570/226

(58) Field of Classification Search
USPC ............................................... 570/226, 227
See application file for complete search history.

(56) References Cited

U.S. PATENT DOCUMENTS 2,725,411 A 11/1955 Ladd et al.
2006/0106263 A1 5/2006 Miller et al.

FOREIGN PATENT DOCUMENTS

WO 2010123148 A1 10/2010

OTHER PUBLICATIONS

Fujimori et al., JP abstract 49066613, Jun. 27, 1974.*
CRC Handbook of Chemistry and Physics, 81st Edition, 2000-2001 (Reference Not Included).
U.S. Appl. No. 61/418,566, filed Dec. 1, 2010.
International Search Report, PCT/US2011/059258/ Filed Nov. 4, 2011, Veronica Suero Gallego.

* cited by examiner

*Primary Examiner* — Jafar Parsa
(74) *Attorney, Agent, or Firm* — Scully, Scott, Murphy & Presser, P.C.

(57) ABSTRACT

Disclosed is a process for the dehydrochlorination of 1,1,1,3-tetrachloropropane comprising contacting 1,1,1,3,tetrachloropropane in the vapor phase in a reaction zone with a catalyst comprising iron, to produce a product mixture comprising 1,1,3-trichloro-1-propene; and recovering said 1,1,3-trichloro-1-propene from the product mixture produced. Also disclosed is a process for the dehydrochlorination of 1,1,1,3-tetrachloropropane comprising heating 1,1,1,3-tetrachloropropane in the liquid phase to produce a mixture comprising 1,1,3-trichloro-1-propene, cooling said mixture, separating hydrogen chloride from said mixture and recovering 1,1,3-trichloro-1-propene.

9 Claims, No Drawings

SYNTHESIS OF 1,1,3-TRICHLORO-1-PROPENE

CROSS REFERENCE(S) TO RELATED APPLICATION(S)

This application claims the priority benefit of U.S. Provisional Application No. 61/418,566, filed Dec. 1, 2010.

BACKGROUND INFORMATION

1. Field of the Disclosure

This disclosure relates in general to methods of synthesis of chlorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

There is also considerable interest in developing new refrigerants with reduced global warming potential for the mobile air-conditioning market.

HFC-1234yf ($CF_3CF=CH_2$) and HFC-1234ze ($CF_3CH=CHF$), both having zero ozone depletion and low global warming potential, have been identified as potential refrigerants. U. S. Patent Publication No. 2006/0106263 A1 discloses the production of HFC-1234yf by a catalytic vapor phase dehydrofluorination of $CF_3CF_2CH_3$ or $CF_3CHFCH_2F$, and of HFC-1234ze (mixture of E- and Z-isomers) by a catalytic vapor phase dehydrofluorination of $CF_3CH_2CHF_2$.

There is a continuing need for more selective and efficient manufacturing processes for the production of HFC-1234yf.

SUMMARY

Disclosed is a process for the dehydrochlorination of 1,1,1,3-tetrachloropropane comprising contacting 1,1,1,3,tetrachloropropane in the vapor phase in a reaction zone with a catalyst comprising iron, to produce a product mixture comprising 1,1,3-trichloro-1-propene; and recovering said 1,1,3-trichloro-1-propene from the product mixture produced.

In another embodiment, disclosed is a process for the dehydrochlorination of 1,1,1,3-tetrachloropropane comprising heating 1,1,1,3-tetrachloropropane in the liquid phase to a temperature of at least 175° C. for at least one hour to produce a product mixture comprising 1,1,3-trichloro-1-propene, cooling said mixture, separating HCl from said product mixture, and recovering 1,1,3-trichloropropene.

The foregoing general description and the following detailed description are exemplary and explanatory only and are not restrictive of the invention, as defined in the appended claims.

DETAILED DESCRIPTION

Disclosed is a process for the dehydrochlorination of 1,1,1,3-tetrachloropropane comprising contacting 1,1,1,3,tetrachloropropane in the vapor phase in a reaction zone with a catalyst comprising iron, to produce a product mixture comprising 1,1,3-trichloro-1-propene; and recovering said 1,1,3-trichloro-1-propene from the product mixture produced.

In another embodiment, disclosed is a process for the dehydrochlorination of 1,1,1,3-tetrachloropropane comprising heating 1,1,1,3-tetrachloropropane in the liquid phase to a temperature of at least 175° C. for at least one hour to produce a product mixture comprising 1,1,3-trichloro-1-propene, cooling said mixture, separating HCl from said product mixture, and recovering 1,1,3-trichloropropene.

1,1,1,3-Tetrachloropropane is readily available from carbon tetrachloride and ethylene. The process disclosed herein are processes to convert 1,1,1,3-tetrachloropropane to 1,1,3-trichloro-1-propene, which can be readily converted to 2,3,3,3-tetrafluoropropene in a few additional steps in high yield and with high selectivity.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

As used herein, inert carrier gas refers to any inert gas which does not participate in the described reaction.

As used herein, a reaction zone is any confined chamber or tube, comprising an inlet and an exit, which can be maintained at a suitable temperature for the process described herein, and which comprises an interior surface which is inert to the starting material, products or by-products.

In one embodiment, 1,1,1,3-tetrachloropropane is dehydrochlorinated to prepare 1,1,3-trichloro-1-propene in the gas phase, in the presence of a catalyst comprising iron. In one embodiment, the catalyst comprises iron wool.

In one embodiment, the process is conducted in a continuous process, in a reaction zone. In another embodiment, the process is conducted on a batch basis. In one embodiment, the reaction zone is a tube reactor packed with catalyst.

In one embodiment, the temperature set point for the reaction zone is set to at least 300° C. In another embodiment, the temperature set point for the reaction zone is set to at least 350° C. In yet another embodiment, the temperature set point for the reaction zone is set to at least 400° C.

In one embodiment, the process is conducted in the presence of a flow of an inert carrier gas. In one embodiment, the carrier gas is selected from nitrogen, argon, helium and xenon. In one embodiment, the carrier gas is nitrogen.

In another embodiment, 1,1,1,3-tetrachloropropane is dehydrochlorinated in the liquid phase. In one embodiment, the reaction is generally performed by heating 1,1,1,3-tetrachloropropane for a period of time in a closed vessel. In one embodiment, the 1,1,1,3-tetrachloropropane is heated to at least 175° C. In another embodiment, the 1,1,1,3-tetrachloropropane is heated to at least 200° C. In one embodiment, the 1,1,1,3-tetrachloropropane is heated to 175° C. for at least one hour. In another embodiment, the 1,1,1,3-tetrachloropropane is heated to 175° C. for at least two hours. In general, shorter reaction times provide lower conversions of starting material, and also result in the formation of smaller amounts of by-products.

In general, the term "batch process" refers to a mode of carrying out a chemical process in which the process begins with the reagents which are reacted under suitable reaction conditions for a suitable time and converted to product. The process is then terminated, and the reaction mixture containing the product is collected. The reaction mixture is typically further processed in order to isolate and or purify the product from unreacted starting materials. On the other hand, the term "continuous process" refers to a mode of carrying out a chemical process in which, once the process has been established, reagents are added to a vessel in which reaction is occurring and products are simultaneously removed. Ideally, a continuous process may be operated to convert a substantially continuous stream of starting materials into a substantially continuous stream of products. "Substantially continuously" or "substantially continuous" when referring to addition of reagents, removal of products or other operations (such as heating, cooling, agitating, etc) performed as a part of chemical processes mean that the operation is carried out over a period of time during the course of the process, in contrast to batch-wise or periodic performance of such operations. The terms are not meant, however, to exclude the possibility of periodic interruption in the operation.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates that the dehydrochlorination of 1,1,1,3-tetrachloropropane over iron catalyst in the gas phase.

A ½" OD×10" tube reactor was packed with 4.4 g of Fe wool that had been pre-cleaned by washing with chloroform. Approximately 5 cc of nichrome helices were placed on top of the Fe wool to act as a vaporizer. A thermocouple was inserted about ½" below the top of the iron. The tube reactor was heated to a temperature between 250° C. and 420° C. under a flow of nitrogen. 1,1,1,3-Tetrachloropropane was fed to the reactor with a syringe pump. Product was collected in 50 mL tubes containing a pH 7 phosphate buffer and analyzed by GC/MS. Contact times ranged from 5 to 7 seconds. Results are summarized in Table 1. Selectivity to 1,1,3-trichloro-1-propene was 99% or greater.

TABLE 1

| Temp actual (° C.) | $N_2$ flow (cc/min) | 1,1,1,3-tetrachloropropane flow rate (mL/min) | % conversion |
|---|---|---|---|
| 290 | 30 | 0.20 | 0.71 |
| 340 | 30 | 0.20 | 13 |
| 390 | 30 | 0.20 | 52.6 |
| 390 | 30 | 0.20 | 43.5 |
| 395 | 30 | 0.20 | 48.5 |
| 393 | 30 | 0.20 | 46.1 |
| 405 | 20 | 0.10 | 61.1 |
| 415 | 25 | 0.20 | 74.7 |
| 416 | 25 | 0.20 | 82.6 |

Example 2

Example 2 demonstrates the dehydrochlorination of 1,1,1,3-tetrachloropropane in the liquid phase.

Into a hastelloy shaker tube was added 40 grams of 1,1,1,3-tetrachloropropane. The tube was sealed, and heated to 175° C. while shaking. After six hours, the tube was cooled to room temperature, and HCl gas was vented off. The remaining organic product mixture was washed with water, and analyzed by GC/MS. Results showed 95% conversion of 1,1,1,3-tetrachloropropane with formation of 80.7% 1,1,3-trichloroprop-1-ene and 19.3% unknowns, which were mostly chlorinated $C_6$ compounds.

Example 3

Example 3 demonstrates the dehydrochlorination of 1,1,1,3-tetrachloropropane in the liquid phase.

Into a hastelloy shaker tube was added 200 grams of 1,1,1,3-tetrachloropropane. The tube was sealed, and heated to 175° C. while shaking. After two hours, the tube was cooled to room temperature, and HCl gas was vented off. The remaining organic product mixture was washed with water, and analyzed by GC/MS. Results showed 71.5% conversion of 1,1,1,3-tetrachloropropane with formation of 69.9% 1,1,3-trichloroprop-1-ene and 1.6% unknowns.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the manufacture of 1,1,3-trichloro-1-propene comprising: (a) contacting 1,1,1,3-tetrachloropropane in the vapor phase in a reaction zone with a catalyst to produce a product mixture comprising 1,1,3-trichloro-1-propene; and (b) recovering said 1,1,3-trichloro-1-propene from the product mixture produced in (a), wherein said catalyst is iron.

2. The process of claim 1, wherein the contacting step is conducted under a flow of an inert carrier gas.

3. The process of claim 2, wherein said inert carrier gas is nitrogen.

4. The process of claim 1, wherein the temperature set point for said reaction zone is at least 300° C.

5. The process of claim 1, wherein the temperature set point for said reaction zone is at least 350° C.

6. A process for the manufacture of 1,1,3-trichloro-1-propene comprising: (a) heating 1,1,1,3-tetrachloropropane in the liquid phase to a temperature of at least 175° C. for at least one hour to produce a product mixture comprising 1,1,3-trichloro-1-propene, (b) cooling said mixture, (c) separating HCl from said product mixture, and (d) recovering 1,1,3-trichloropropene.

7. The process of claim 6, wherein the selectivity for producing 1,1,3-trichloro-1-propene is at least 90%.

8. The process of claim 6, wherein the selectivity for producing 1,1,3-trichloro-1-propene is at least 95%.

9. The process of claim 1 wherein the catalyst is iron wool.

* * * * *